(12) United States Patent
Hardy (10) Patent No.: US 8,104,487 B2
(45) Date of Patent: Jan. 31, 2012

(54) DENTAL FLOSS HOLDER

(76) Inventor: Richard Hardy, Seattle, WA (US)

( * ) Notice: Subject to any disclaimer, the term of this patent is extended or adjusted under 35 U.S.C. 154(b) by 0 days.

(21) Appl. No.: 12/709,449

(22) Filed: Feb. 19, 2010

(65) Prior Publication Data

US 2011/0203609 A1    Aug. 25, 2011

(51) Int. Cl.
*A61C 15/04* (2006.01)
(52) U.S. Cl. ...................................................... 132/323
(58) Field of Classification Search .................. 132/323, 132/309, 321, 324–329; 206/63.5; 242/169, 242/227, 570, 586.1; D28/66, 68
See application file for complete search history.

(56) References Cited

U.S. PATENT DOCUMENTS

| | | | |
|---|---|---|---|
| 1,260,011 A | 3/1918 | Muchow | |
| 1,570,357 A * | 1/1926 | Lawrenz | 132/324 |
| 1,700,550 A | 1/1929 | Stafford | |
| 2,217,917 A * | 10/1940 | Munro | 132/326 |
| 2,492,291 A * | 12/1949 | Johnson | 132/324 |
| 2,828,754 A * | 4/1958 | Stewart | 132/323 |
| 2,873,749 A * | 2/1959 | Gjerde | 132/323 |
| 3,759,274 A | 9/1973 | Warner | |
| 3,766,931 A | 10/1973 | Fielder | |
| 3,858,594 A * | 1/1975 | Ensminger | 132/325 |
| 3,871,393 A * | 3/1975 | Wharton | 132/326 |
| 3,908,677 A | 9/1975 | Beach | |
| 3,949,769 A | 4/1976 | Minka | |
| 3,998,236 A | 12/1976 | Koo | |
| 4,004,599 A | 1/1977 | Risenfeld | |
| 4,031,909 A | 6/1977 | Kelley | |
| 4,052,994 A | 10/1977 | Thun | |
| D251,859 S | 5/1979 | Kent | |
| 4,254,786 A | 3/1981 | Won | |
| 4,727,895 A * | 3/1988 | Berarducci | 132/323 |
| 4,901,742 A * | 2/1990 | Olson | 132/325 |
| 4,936,326 A | 6/1990 | Eckroat | |
| 4,995,361 A | 2/1991 | Lorenzana et al. | |
| 5,094,256 A * | 3/1992 | Barth | 132/322 |
| 5,176,157 A | 1/1993 | Mazza | |
| 5,188,133 A | 2/1993 | Romanus | |
| 5,201,330 A | 4/1993 | Won | |
| 5,232,002 A * | 8/1993 | McClallen | 132/325 |

(Continued)

FOREIGN PATENT DOCUMENTS

CA    2343140 A1    3/2000

(Continued)

OTHER PUBLICATIONS http://en.wikipedia.org/wiki/Tension_%28physics%29 (2 pages).

(Continued)

*Primary Examiner* — Todd Manahan
*Assistant Examiner* — Vanitha Elgart
(74) *Attorney, Agent, or Firm* — R. Reams Goodloe, Jr.

(57) ABSTRACT

A dental floss holder. The dental floss holder includes a body having a spool case for holding a length of dental floss, a cover for the spool case, a neck extending from the spool case along a first axis, and first and second fingers extending outward from said neck at an arcuate angle. In an embodiment, the fingers may be parallel. A manually engageable clamp is provided with threaded fastener that engages a threaded nut having a compressing flange, so that the compressing flange works against a land provided on the outside of the cover. A pivot post is provided to prevent dental floss from becoming entangled with the threads of the fastener.

37 Claims, 7 Drawing Sheets

U.S. PATENT DOCUMENTS

| | | | | |
|---|---|---|---|---|
| 5,253,662 | A | | 10/1993 | Won |
| 5,269,331 | A | | 12/1993 | Tanriverdi |
| 5,280,797 | A | * | 1/1994 | Fry .................. 132/323 |
| 5,417,232 | A | | 5/1995 | Ballard |
| 5,503,169 | A | | 4/1996 | Won |
| 5,573,021 | A | * | 11/1996 | Grofcisk et al. ....... 132/324 |
| 5,664,592 | A | * | 9/1997 | Regnier ............ 132/325 |
| 5,678,578 | A | | 10/1997 | Kossak et al. |
| 5,947,133 | A | | 9/1999 | Kossak et al. |
| 6,092,536 | A | | 7/2000 | Owens |
| 6,123,087 | A | * | 9/2000 | Jang ................. 132/325 |
| 6,161,556 | A | * | 12/2000 | Gutierrez ........... 132/327 |
| 6,164,294 | A | * | 12/2000 | Takabu .............. 132/327 |
| 6,474,347 | B1 | * | 11/2002 | Hallinder et al. ..... 132/325 |
| 7,082,950 | B2 | | 8/2006 | Kossak et al. |
| 7,305,997 | B2 | * | 12/2007 | Liu et al. ........... 132/325 |
| 7,631,650 | B2 | | 12/2009 | Major |
| 7,882,845 | B2 | * | 2/2011 | Filsouf ............. 132/323 |
| 2004/0244814 | A1 | * | 12/2004 | Prineppi ............ 132/322 |
| 2004/0244815 | A1 | * | 12/2004 | Lee ................. 132/323 |
| 2004/0255972 | A1 | * | 12/2004 | Chen ................ 132/325 |
| 2005/0092347 | A1 | * | 5/2005 | Fan ................. 132/325 |
| 2006/0011211 | A1 | * | 1/2006 | Landry .............. 132/325 |
| 2008/0149134 | A1 | * | 6/2008 | Crossman ........... 132/324 |
| 2008/0289648 | A1 | * | 11/2008 | Liu ................. 132/322 |
| 2009/0301514 | A1 | | 12/2009 | Passafaro |
| 2010/0006120 | A1 | | 1/2010 | Shen et al. |
| 2011/0041870 | A1 | * | 2/2011 | Kalbfeld et al. ...... 132/325 |

FOREIGN PATENT DOCUMENTS

| | | |
|---|---|---|
| CA | 2343140 | 8/2005 |
| EP | 0235518 A1 | 1/1987 |
| EP | 0379504 B1 | 12/1993 |
| WO | WO 97/48349 | 12/1997 |

OTHER PUBLICATIONS http://en.wikipedia.org/wiki/Compression_%28physical%29 (2 pages).

Webster's New World Dictionary of the American Language, by the World Publishing Company, Copyright 1951 (4 pages) (pp. 301 and 1502) with cover sheet and copyright details).

* cited by examiner

DENTAL FLOSS HOLDER

COPYRIGHT NOTICE

A portion of the disclosure of this patent document contains drawing materials that are subject to copyright protection. The patent owner has no objection to the facsimile reproduction by anyone of the patent document or the patent disclosure, as it appears in the Patent and Trademark Office patent file or records, but otherwise reserves all copyright rights whatsoever.

TECHNICAL FIELD

This invention relates to dental floss holders, and more particularly to manually operated dental floss holders.

BACKGROUND

Many types of dental floss holders have been proposed or used, both for storing dental floss and for positioning dental floss in a relatively secure, effective, usable configuration. However, available versions known to me are not configured in a simple, easily manually adjustable manner that positions dental floss in a secure, tensioned position, adaptable for simple replenishment of a used, worn out section of floss with a new, unused section of floss after each use.

Various prior art dental floss holders have adopted certain technological features. However, in the various prior art devices known to me, there are a variety of defects, some significant, with respect to the ability of the average user or consumer to manually secure new floss in an easily tensionable manner after removing and/or discarding used floss. Mechanisms for providing tension in a section of floss for use is always somewhat problematic in dental floss holders, since dental floss is generally provided with some type of wax or other relatively slippery constituent or coating, to enhance performance and passage through tight fitting passageways between teeth of the user.

In some prior art dental floss holder designs, a spool or other floss holder is provided, but in such designs, the floss holder itself is held in manner that tension is created relative to the floss on the spool. Thus, securing the spool itself, and keeping it from turning, is critical to maintaining tension in the active flossing section in such designs, even though such section is spaced well away from the floss spool itself. In other designs, use of cleats or tie-off posts is relied upon to provide tension in the working floss section. However, such devices are not particularly reliable. Other prior art designs rely on knotting or tie-off of floss, once it has been pulled into position. Yet other prior art designs require pressure against levers or other mechanisms to be maintained during flossing, in order to maintain tension of the working portion of the dental floss. Such designs are difficult for some users to properly manipulate. Still other designs require multiple floss reels, typically one for new floss supply and one for used floss storage.

Thus, in spite of the extensive body of prior art for dental floss holders and applicators, there still remains an as yet unmet need for a dental floss holder that can easily and readily be manually adjusted to secure tension in a working floss section. It would be especially helpful if tension could be maintained in a section of dental floss during use without the need for a user to apply force or pressure to a tool mechanism included in the floss holder. Such a dental floss holder would be of particular benefit to those users who have relatively weak gripping hands, such as injured, infirm, and older users.

Moreover, a new dental floss holder that avoids the requirement for multiple spools, or parts inherent in the use or adjustment of the same, should benefit the manufacturer, and ultimately the user, as fewer parts would be required. Thus, an exemplary design ideally would be capable of being manufactured and marketed at lower cost than many prior art dental floss holders. Since many prior art systems do not adequately address the tensioning issue, there remains a significant and as yet unmet need for a simple dental floss holder that can easily and efficiently provide tension to a working section of dental floss.

SUMMARY

I have now developed a manually tensionable dental floss holder. The device can be easily and quickly manually adjusted to remove used floss and to secure new floss in its place. Further, the device avoids the need to apply tension against, or to restrict movement of, a spool supplying new floss, or of a spool taking up used floss.

The dental floss holder includes a body that provides a spool case for holding a spool of dental floss of selected diameter. The spool case has a floor, and in an embodiment, sidewalls. Extending outward from the spool case along a first longitudinal axis is a neck. Spaced apart first and second fingers extend outwardly from the neck. The first finger extends outward from the neck along a second longitudinal axis. The second longitudinal axis is offset from the first longitudinal axis by an angle alpha ($\alpha$). The second finger extends outward from the neck along a third longitudinal axis. The third longitudinal axis is offset from the first longitudinal axis by an angle beta ($\beta$). In an embodiment, the first and second longitudinal axes are parallel, and thus, angle alpha ($\alpha$) and angle beta ($\beta$) are equal. In an embodiment, the neck is substantially coplanar with the first finger. In an embodiment, the neck is substantially coplanar with the second finger. Each of the first and second fingers extend outwardly from the neck to a respective distal end. Along at least a portion of the distal end of the first finger, a first floss guide is provided. Along at least a portion of the distal end of the second finger, a second floss guide is provided. The first finger extends back toward the neck from its distal end to a knuckle. The knuckle provides a transition from the neck to the first finger. At the outer surface of the knuckle, a knuckle floss guide is provided. Moving further rearward from the knuckle toward the spool case, an arcuate neck surface is provided, complementary in shape to a users thumb. The arcuate neck surface is adapted to provide space for the thumb (or index finger, depending on how the dental floss holder is manipulated by a user) to engage and tension a length of dental floss operably positioned between the knuckle and a first tensioning ledge. The second finger extends from its distal end back toward the neck to a bight. The bight provides a transition from the neck to the second finger. The bight is sized and shaped complementary to a human thumb, so as to accommodate thumb tensioning motion against a length of floss operably positioned between the second finger and a second tensioning ledge. It should be noted that such bight size and shape is also complementary to a human index finger, so as to accommodate tensioning motion against a length of floss operably positioned between the second finger and a second tensioning ledge.

The dental floss holder also includes a cap that is shaped to at least partially cover a spool case. In an embodiment, spaced apart first and second tensioning ledges are integrally formed with and provided with the cap as a one-piece molded part. In an embodiment, the first and second tensioning ledges are provided at opposing positions spaced apart along a fourth axis. In an embodiment, the fourth axis is not orthogonal to the first longitudinal axis of the neck. In an embodiment, the cap further includes a floss dispensing slot. In an embodiment, the floss dispensing slot may be located at an edge of the cap near the neck. The floss dispensing slot provides access between a spool of dental floss in the spool case and a clamp, so that dental floss may be withdrawn from the spool case for use, and easily secured at a clamp. In an embodiment, a dental floss cutter may be provided to cut a length of dental floss at a desired length, which is usually to cut off a section of floss that has been used, and to enable the user to secure a new length of floss between the first and second fingers, ready for use.

In an embodiment, the clamp included with the dental floss holder includes a compressing flange adapted for compressing, by manual action on a grip, a length of dental floss, and thus securing such length of dental floss against movement through the clamp during the use of said dental floss holder, so as to maintain a properly tensioned length of dental floss between the first and second fingers. In an embodiment, the cap may provide, on an outer surface, an annular shaped pivot post upwardly protruding therefrom for a height $H_1$ and on which a nut, provided as part of a clamp design, can turn. In an embodiment, the height $H_1$ may be provided at about three times or more the effective diameter D of a length of dental floss for use in said apparatus. Although not all floss is cylindrical, for trouble free operation, in an embodiment, such a pivot post is advantageous when it effectively prevents the dental floss being used from escaping, near the center of rotation of the nut, the gap between the compressing flange for the land on which the clamp operates (which may be the top of the cap). In an embodiment, the nut may be secured by a threaded fastener. In such an embodiment, the user turns the nut, using an upwardly protruding grip on the nut, to secure the compressing flange of the nut downward toward a land on the outer surface of the cap, and in doing so, compressing a section of dental floss to secure it against movement.

In an embodiment, the spool of dental floss may be replaceable. In an embodiment especially useful for many average users or consumers, an easily tightenable nut with a grip, such as a wing nut having easily manually engageable purchase lands, may be provided. In such a manner, when using a screw fastener, the action of the user against the grip rotates the nut, which translates such circular motion into the application of pressure via flanged portions of the nut against a portion of floss, to frictionally engage a section of floss between the nut flange and a land, to securely locate the floss beneath the nut, and thus securely locate a working section of dental floss in a working location in the dental floss holder. Consequently, the working section of dental floss is easily and quickly manually secured for use.

The foregoing briefly describes certain aspects and elements of an exemplary dental floss holder, and various components thereof. The various objectives, features and advantages of the invention(s) will be more readily understood upon consideration of the detailed description, taken in conjunction with careful examination of the accompanying figures of the drawing.

BRIEF DESCRIPTION OF DRAWING

In order to enable the reader to attain a more complete appreciation of the invention, and of the novel features and advantages thereof, attention is directed to the following detailed description when considered in connection with the accompanying drawings, wherein.

In the various figures of the drawing, like features may be illustrated with the same reference numerals, without further mention thereof. Further, the drawing figures are merely exemplary, and may contain various elements that might be present or omitted from actual implementations of various embodiments depending upon the circumstances. An attempt has been made to draw the figures in a way that illustrates at least those elements that are significant for an understanding of the various embodiments and aspects of the invention. However, other elements or functional components for a dental floss holder, as well as different embodiments of artistic elements such as a shape of components or visual design of various elements, may be utilized in order to provide a useful, adjustable, and reliable dental floss holder.

DETAILED DESCRIPTION

Figure 1:
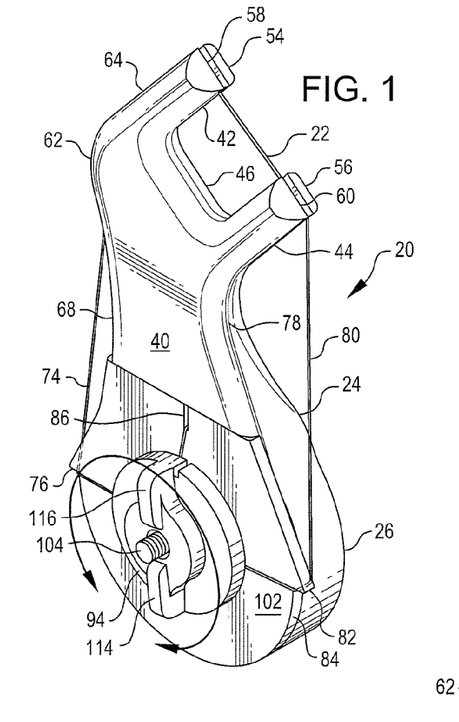
FIG. 1 provides a side perspective view of schematic view of an embodiment for a dental floss holder, showing the device with a working length of dental floss located between first and fingers, and with the dental floss tensioned via first and second tensioning ledges and secured at a clamp, which clamp is provided by a nut having a lower compressing flange and an upwardly protruding grip for turning the nut and securing the nut against the outer surface of a cover via a threaded fastener.
Figure 2:
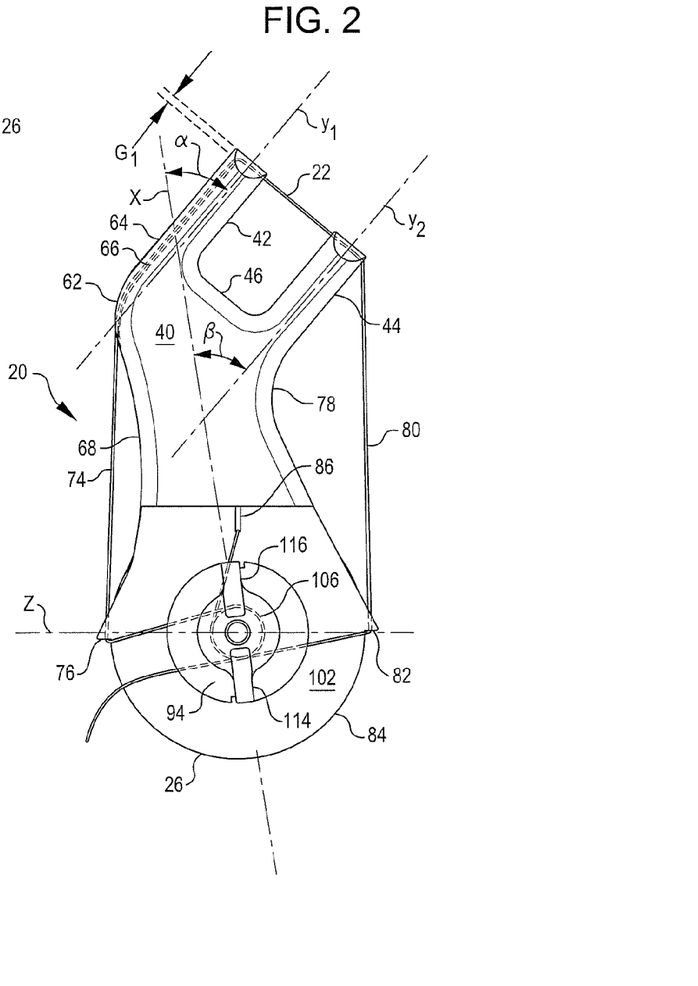
FIG. 2 is a top plan view showing the obverse side of the embodiment for a dental floss holder just shown above in FIG. 1, now further showing the use of a floss dispensing slot in the cover, as well as a path for a length of floss in a first method of use, showing the floss exiting the dispensing slot, going around the pivot post, then out to a second tensioning ledge, up to a second finger, across to a first finger, then out to a knuckle, then down to a first tensioning ledge, and thence back to and around the pivot post, below the compressing flange of the nut provided as part of the grip.
Figure 3:
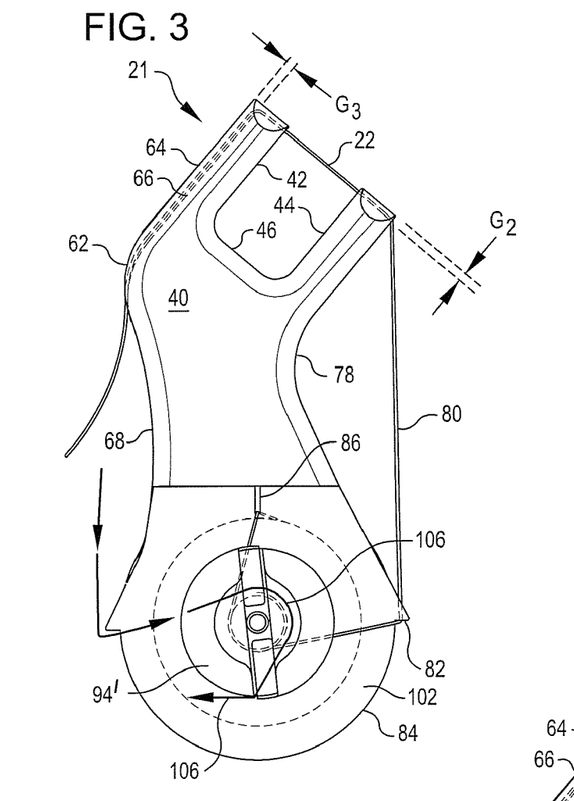
FIG. 3 is similar to the embodiment just shown in FIG. 2, but now shows the use of another embodiment for the nut used as part of the grip, and in particular, illustrates how a length of dental floss may be wrapped to gain additional mechanical advantage from the nut, using notches provided on the nut.
Figure 4:
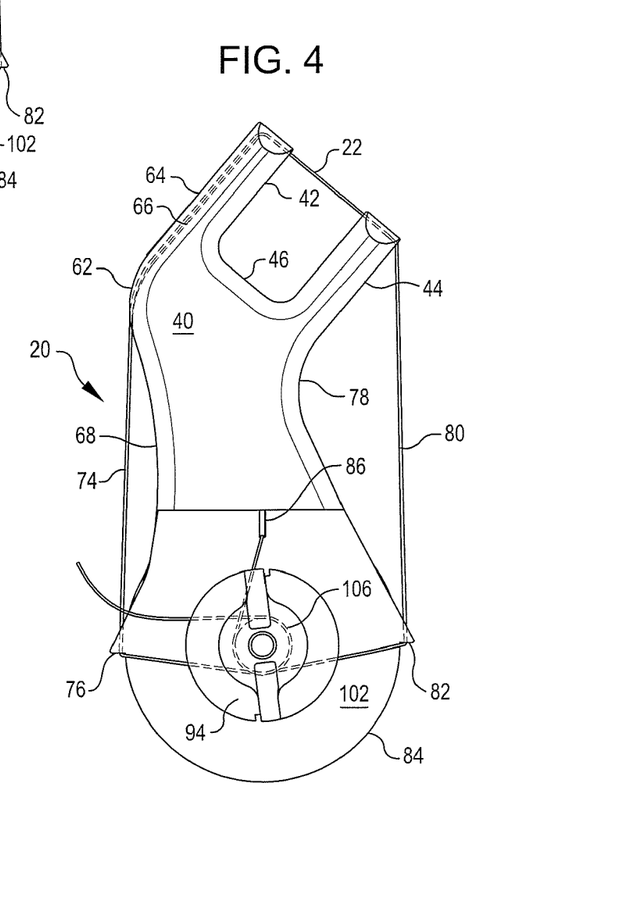
FIG. 4 is similar to the embodiment just shown in FIG. 3, but now shows the practice of a different method for securing a section of dental floss than that just illustrated in either FIG. 2 or in FIG. 3, and indicates that the clamp and manual tensioning provisions provided may be effective with dental floss even when winding dental floss around the pivot post in a counterclockwise manner (as seen in this FIG. 4), even though contrary to the usual method in the clockwise direction (as seen in FIG. 2) wherein friction between dental floss and a compressing flange of the nut tends to urge the dental floss to be tightened.
Figure 5:
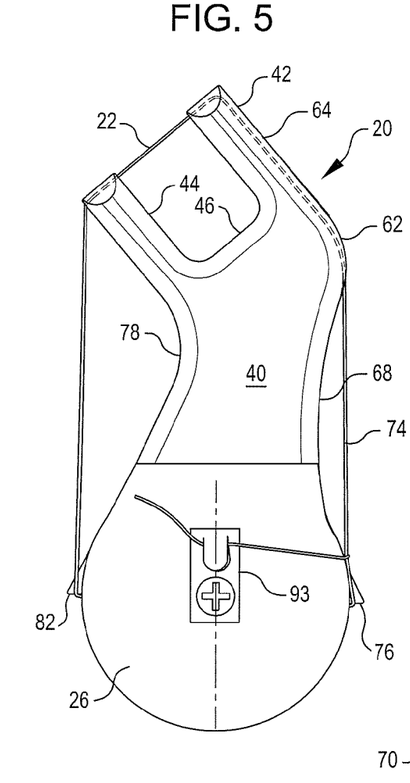
FIG. 5 is a bottom plan view showing the reverse side of the embodiment for a dental floss holder just shown above in FIG. 1, now further showing details of the first and second tensioning ledges, and well as a dental floss cutter.

Attention is directed to FIG. 1 of the drawing, wherein various features of an embodiment for a dental floss holder 20 are shown. The dental floss holder 20 is adapted for positioning a length of dental floss 22 for use in flossing of teeth by a user of the dental floss holder 20. A similar (but slightly different) embodiment for a dental floss holder 21 is shown in FIGS. 3, 7, 10, and 12, as will be further explained herein below. However, through-out the various drawing figures, like structures will be indicated by like reference numerals.

The dental floss holder 20 includes a body 24 that includes a spool case 26 for holding a spool 28 (see FIGS. 7 and 8) of dental floss 30 of selected effective diameter D, as further discussed below. The spool case 26 has a bottom 31 with floor 32. In an embodiment, sidewalls 34 having an interior wall 36 and an exterior wall 38 are provided. Extending outward from the spool case 26 generally along a first longitudinal axis indicated by reference letter X is a neck 40. Spaced apart first 42 and second 44 fingers extend outwardly from the neck 40. In an embodiment, a generally U-shaped working structure 46 is provided for the extension of first 42 and second 44 fingers.

In an embodiment, the first finger 42 extends outward from the neck 40 along a second longitudinal axis indicated by reference letter $Y_1$. The second longitudinal axis $Y_1$ is offset from the first longitudinal axis X by an angle alpha ($\alpha$). The second finger 44 extends outward from the neck 40 along a third longitudinal axis indicated by reference letter $Y_2$. The third longitudinal axis $Y_2$ is offset from the first longitudinal axis X by an angle beta ($\beta$). In an embodiment, the first $Y_1$ and second $Y_2$ longitudinal axes are parallel, and thus, angle alpha ($\alpha$) and angle beta ($\beta$) are equal. In an embodiment, angle alpha ($\alpha$) and angle beta ($\beta$) are acute angles.

Figure 12:
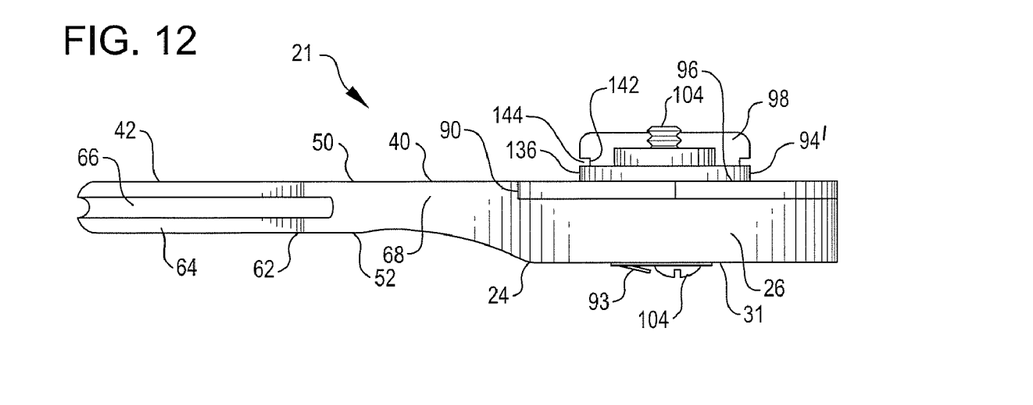
FIG. 12 is a side elevation view of an embodiment for a dental floss holder, showing the spool case portion of the body, the curved tapered portion of the neck, and the knuckle and floss guides and the first finger, as well as a cap with threaded fastener at the center, and a nut with compressing flange and manual grip.

With reference to FIGS. 1 and 12, it can be appreciated that the body 24 has an obverse surface 50, and a reverse surface 52. In FIG. 12, it can be seen that in an embodiment, the neck 40 may be substantially coplanar with the first finger 42. And, in FIG. 1 and various other figures, it can be seen that in an embodiment, the neck 40 may be substantially coplanar with the second finger 44.

In an embodiment, the neck 40 may be tapered, to bring closer together the obverse surface 50 and the reverse surface 52 of neck 40, so that the neck 40 decreases in thickness outward from the spool case 26 toward the first 42 and second 44 fingers. In an embodiment the tapering may be achieved by concave shaping of the reverse surface 52 of neck 40 to provided a curved reverse surface 52 of neck 40.

Returning now to FIG. 1, it can be seen that in an embodiment, the first 42 and second 44 fingers extend outwardly from the neck 40 to respective distal ends 54 and 56. Along at least a portion of the distal end 54 of the first finger 42, a first floss guide 58 is provided The first floss guide 58 may be provided as a groove of depth $G_1$. Along at least a portion of the distal end 56 of the second finger 44, a second floss guide 60 is provided. The second first floss guide 60 may be provided as a groove of depth $G_2$.

The first finger 42 extends back toward the neck 40 from its distal end 54 to a knuckle 62. The knuckle 62 provides a transition from the neck 40 to the first finger 42. Along the outer surface 64 of first finger 42, a knuckle floss guide 66 is provided. The knuckle floss guide 66 may be provided as a groove of depth $G_3$.

Figure 6:
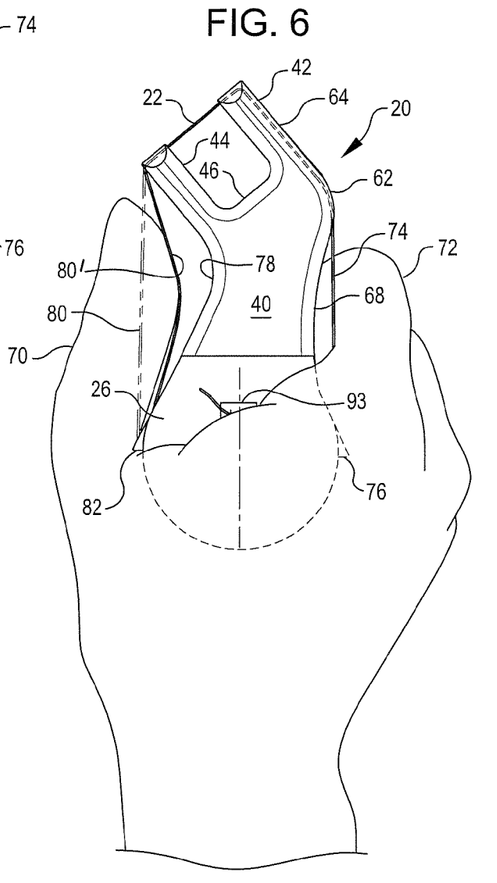
FIG. 6 is a partial bottom plan view showing the reverse side of the embodiment for a dental floss holder as just shown in FIG. 5, now further showing details of one user grip for use in a method of manually tensioning a length of dental floss by use of a thumb.
Figure 11:
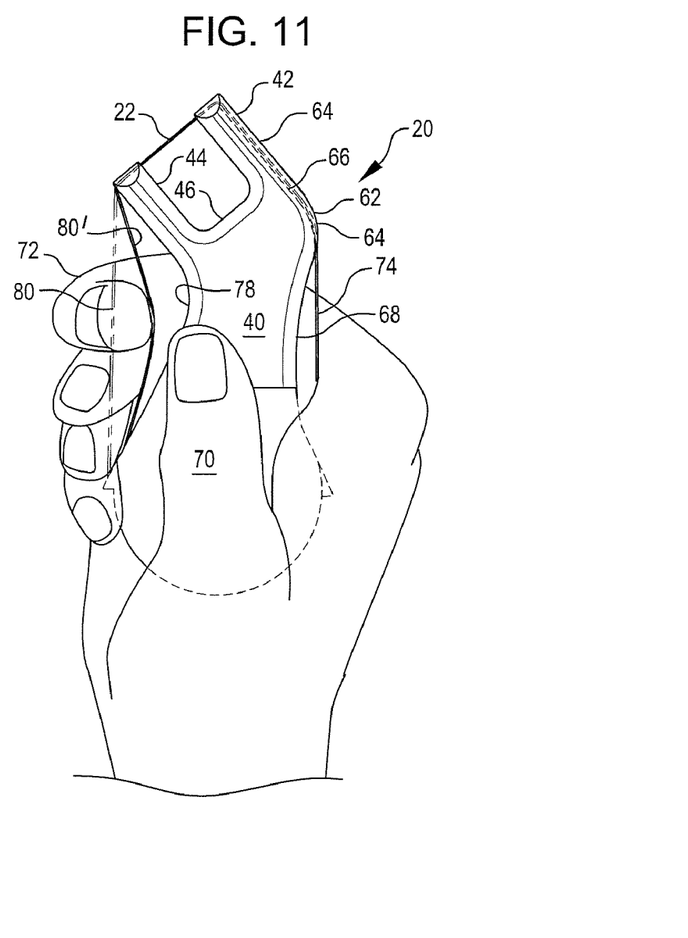
FIG. 11 is a partial top plan view showing the obverse side of the embodiment for a dental floss holder as just shown in FIG. 10, now further showing details of another user grip for use in a method of manually tensioning a length of dental floss by use of a user's finger.

Moving further rearward from the knuckle 62 toward the spool case 26, an arcuate neck surface 68 is provided, complementary in shape to a users thumb 70. The arcuate neck surface 68 is adapted to provide space for the thumb 70 (or index finger 72, as illustrated in FIGS. 6 and 11, depending on how the dental floss holder 20 or 21 is manipulated by a user) to engage and tension a length 74 of dental floss operably positioned between the knuckle 62 and a first tensioning ledge 76.

The second finger 44 extends from its distal end 56 back toward the neck 40 to a bight 78. The bight 78 provides a transition from the neck 40 to the second finger 44. As illustrated in FIG. 6, the bight 78 is sized and shaped complementary to a human thumb 70, so as to accommodate thumb 70 tensioning motion against a second length of dental floss 80 operably positioned between the second finger 44 and a second tensioning ledge 82. In this manner, the second length of dental floss 80 (shown in broken lines in FIGS. 6 and 11) may be moved to position indicated in FIGS. 6 and 11 to be the location of dental floss 80', which increases tension on the working length of dental floss 22. In an embodiment, the size and shape of bight 78 is also complementary to a human index finger 72, so as to accommodate tensioning motion against the second length of dental floss 80 operably positioned between the second finger 44 and a second tensioning ledge 82.

In an embodiment, the dental floss holder 20 also includes a cap 84 that is shaped to at least partially cover the spool case 26. In an embodiment, spaced apart first 76 and second 82 tensioning ledges are integrally formed with and provided with the cap 84 as a one-piece molded part. In an embodiment, the first 76 and second 82 tensioning ledges are provided at opposing positions laterally spaced apart on cap 84 along a fourth axis indicated by reference numeral Z. In an embodiment, the fourth axis Z is near to (but not precisely) orthogonal to the first longitudinal axis X of the neck 40. In an embodiment, the cap 84 further includes a floss dispensing slot 86 defined by slot edgewalls 88. In an embodiment, the floss dispensing slot 86 may be located at an upper edge 90 of the cap 86 near the neck 40. The floss dispensing slot 86 provides access between a spool 28 of dental floss 30 in the spool case 26 and a clamp 92, so that dental floss 30 may be withdrawn from the spool case 26 for use, and easily secured at a clamp 92. In an embodiment, a dental floss cutter 93 may be provided to cut a length of dental floss 30 at a desired length, which is usually to cut off a section of dental floss that has been used, and to enable the user to secure a new length of floss 22 between the first 42 and second 44 fingers, ready for use. In an embodiment, the dental floss cutter 93 may be affixed to the spool case 26.

Figure 8:
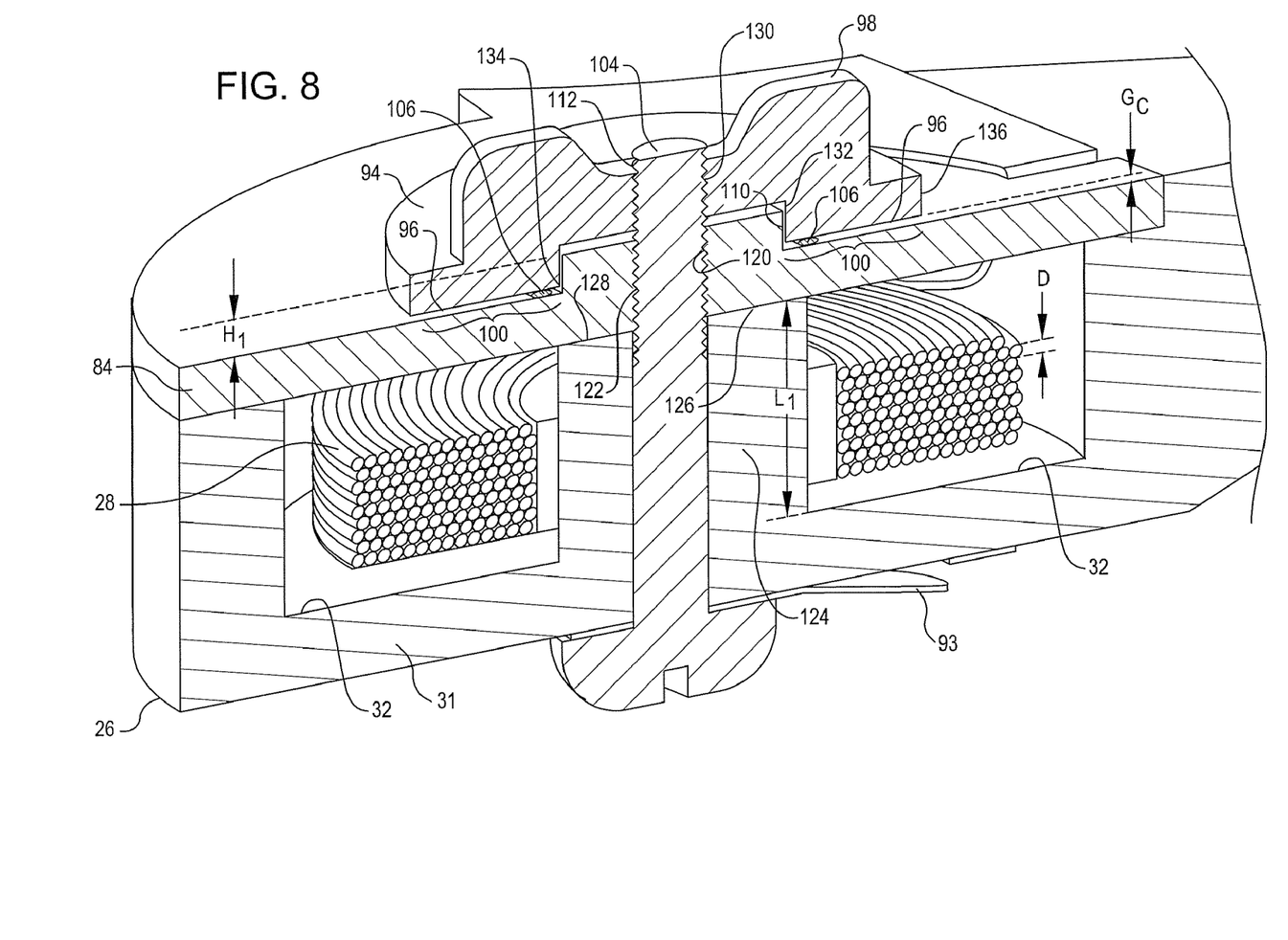
FIG. 8 shows a perspective cross-sectional view of the certain components of an embodiment for a dental floss holder, including the spool case portion of the body, with the start of the tapering portion of the neck, as well as a spool of dental floss in the spool case, and cap with upwardly protruding pivot post at the center, as well as a threaded fastener, and a nut with compressing flange and manual grip.

In an embodiment, the clamp 92 included with the dental floss holder 20 or 21 includes a nut 94 (or nut 94' with certain enhancements as further described below) with compressing flange 96 adapted for compressing, by manual action using a grip 98 on nut 94, a land 100 on outer surface 102 of cap 84, and threaded fastener 104, to cooperatively secure a section of dental floss 106, as shown in FIG. 8. In this manner, the section of dental floss 106 is secured against movement through the clamp 92 during the use of the dental floss holder 20 or 21, so as to maintain a properly tensioned length of dental floss 22 between the first 42 and second 44 fingers. In an embodiment, the cap 84 may provide, on outer surface 102, an annular shaped pivot post 110 upwardly protruding therefrom for a height $H_1$ and on which nut 94, provided as part of the clamp 92, can turn. In an embodiment, the height $H_1$ may be provided at about three times or more the effective diameter D of a length of dental floss for used in said apparatus. Various types of dental floss are not cylindrical as is the floss shown in FIG. 8, and thus such alternative floss supplies may have an "effective diameter D" related to a thickness of a particular dimension encountered in a non-circular floss embodiment. For trouble free operation, in an embodiment, such a pivot post 110 is advantageous when it effectively prevents the dental floss being used, regardless of shape, from escaping (near the center of rotation of the nut 94 adjacent threads 112 of threaded fastener 104), the gap $G_c$ existing between the compressing flange 96 and the land 100 on which the clamp 92 operates (which may be the outer surface 102 of the cap 84). In an embodiment, it may be advantageous for the pivot post 110 to be provided in a configuration such as that illustrated herein to prevent dental floss from becoming entangled with the threads 120 (further discussed below) of the fastener 20 or 21. In an embodiment, the nut 94 may be secured by the threaded fastener 104, as noted above. In such an embodiment, the user turns the nut 94, using the upwardly protruding grip 98 on the nut 94, to secure the compressing flange 96 of the nut 94 downward toward the land 100 on the outer surface 102 of the cap 84, and in doing so, compresses a section of dental floss 106 to secure it against movement.

In an embodiment, the spool 28 of dental floss 30 may be disposable. In an embodiment, a similar spool 28 of dental floss may be replaceable. In an embodiment especially useful for many average users or consumers, an easily tightenable nut 94 or 94', with a grip 98, such as a wing nut configuration having easily manually engageable purchase lands 114 and 116, may be provided. In such a manner, when using a threaded fastener 104, the action of the user against the grip 98 rotates the nut 94, which translates such circular motion into the application of pressure via compressing flange 96 of the nut 94 or 94' against a section of floss 106, to frictionally engage such section of floss 106 between the compressing flange 96 and land 100, to securely locate the section of floss 106 beneath the nut 94 or 94' and thus securely locate a working section of dental floss 22 in a working location in the dental floss holder 20 or 21. Consequently, the working section of dental floss is easily and quickly manually secured for use.

As depicted in FIG. 8, in an embodiment, the pivot post 110 may include annular threads 120 therein. Such threads 120 are complementary to threads 112 on fastener 104. In this manner, fastener 104 may also be used to affix cap 84 to body 24 and, in an embodiment, securely cover spool case 26. In an embodiment, the pivot post 110 may be provided integrally formed with the cap 84 in a one-piece configuration. Also, in an embodiment, the cap 84 may further include a threaded bore 122 concentric with the threads 120 within the pivot post 110.

Figure 7:
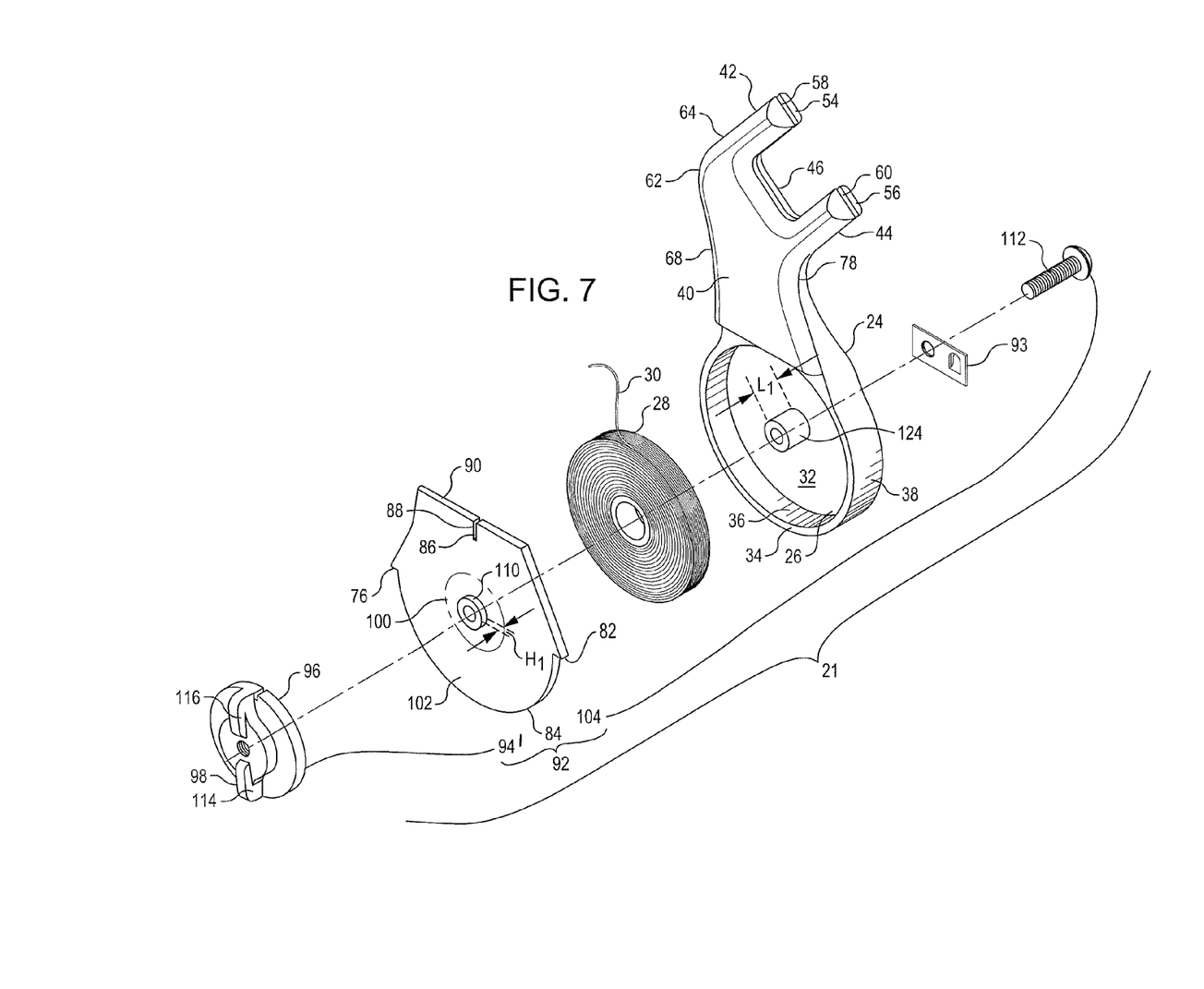
FIG. 7 shows an exploded perspective view of the various components of an embodiment for a dental floss holder, including a body with spool case, and a spool of dental floss therein, neck extending therefrom, and a pair of fingers extending outwardly from the neck at an angle to the longitudinal axis of the neck, a cap with first and second tensioning ledges on opposing edges and a pivot post at the center, and near the neck, a floss dispensing slot, as well as a threaded fastener, dental floss cutter, and a nut with compressing flange and manual grip.

In an embodiment, as seen for example in FIG. 7, a spool post 124 may also be provided. A spool post 124 may be sized and shaped for accommodating the spool 28 of dental floss 30 for rotary movement of the spool 28 about the spool post 124. In an embodiment, the spool post 124 may be provided as a annular shaped structure of length $L_1$. The spool post 124 extends upward from the floor 32 to an upper surface 126 sized and shaped for securing mating engagement with a lower side 128 of cap 84. In an embodiment, the upper surface 126 of the spool post 126 is provided as a flat surface adapted for support of lower side 128 of cap 84.

Figure 9:
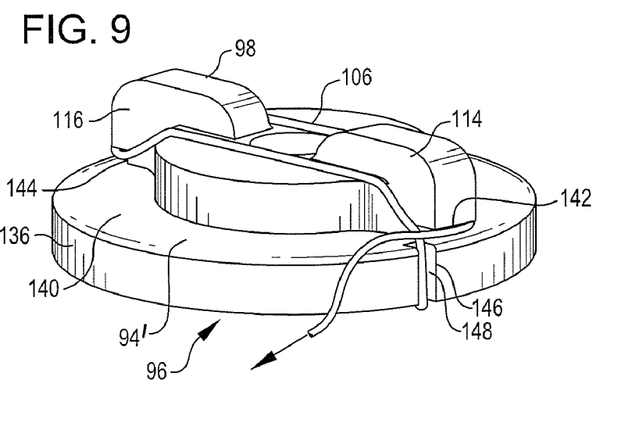
FIG. 9 shows a perspective view of yet another embodiment for a nut to be used as part of a clamp, here showing where the nut includes an outer sidewall, and an upper flange surface, and where the grip portion is affixed at least in part to the upper flange surface, and showing the location adjacent the outer sidewall where an undercut floss tensioning notch is provided, and where a vertically extending floss receiving notch defined by floss receiving notch edgewalls is provided, and further illustrating a path for dental floss to be wound using one method of tightening dental floss that might be useful when employing the dental floss holder.
Figure 10:
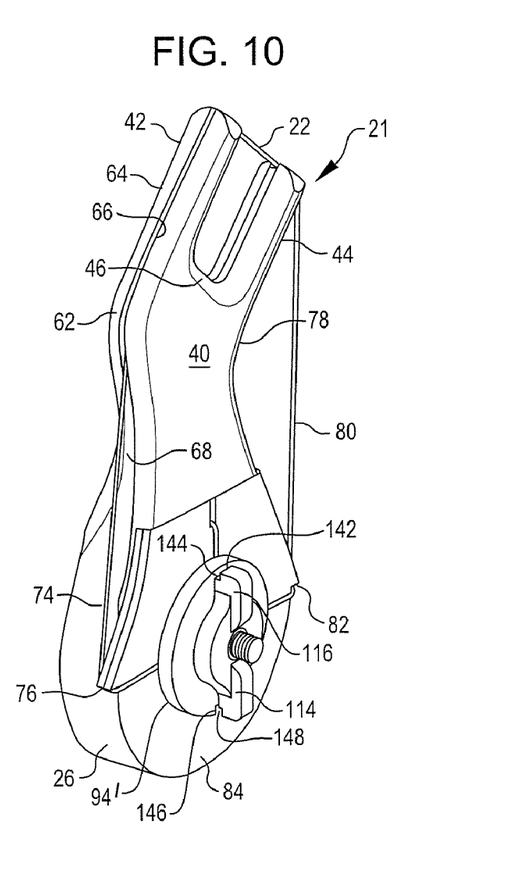
FIG. 10 provides a side perspective view of schematic view of an embodiment for a dental floss holder, similar to the embodiment just illustrated in FIG. 9, showing the device with a working length of dental floss located between first and second fingers, and with the dental floss tensioned via first and second tensioning ledges and secured at a clamp, which clamp is provided by a nut having a lower compressing flange and an upwardly protruding grip for turning the nut and securing the nut against the outer surface of a cover via a threaded fastener, and where the nut further includes an undercut floss tensioning notch and a vertically extending floss receiving notch.

Turning again to FIGS. 8 and 9, it can be appreciated that in an embodiment, the clamp 92 includes threaded fastener 104, and nut 94 or 94' having threads 130 complementary to threads 112 on fastener 104, and adapted for tightening the nut 94 or 94' with respect to fastener 104. In an embodiment, the nut 94 or 94' includes a shoulder portion 132 complementary at least in part in size and shape to the pivot post 110. In an embodiment, the compressible flange 96 extends outward from the lower corner 134 of the shoulder portion 132.

In an embodiment, nut 94 (or nut 94' as seen in FIGS. 3, 7, 9, 10, and 12), the nut 94 or 94' may include an outer sidewall 136 generally circular in shape. In an embodiment, the nut 94 or 94' may include an upper flanged surface 140, and in such cases, the grip 98 is affixed at least in part to the upper flanged surface 140. In nut 94', adjacent the outer sidewall 136, an undercut floss tensioning notch 142, defined by tensioning notch sidewalls 144, may be provided between said the grip 98 and the upper flanged surface 140. Additionally, in an embodiment, the outer sidewall 136 may include a vertically extending floss receiving notch 146 defined by floss receiving notch edgewalls 148.

In an embodiment, it may be advantageous to provide the components of the dental floss holder 20 or 21 as injection molded components. In an embodiment, a suitable moldable compound such as the thermoplastic polyethylene may be utilized. In various embodiments, high density polyethylene (HDPE), or high-modulus polyethylene (HMPE), or high performance polyethylene (HPPE), or ultrahigh molecular weight polyethylene (UHMWPE) may be utilized. Ideally, in an embodiment, the selected moldable compound ideally would be odorless, tasteless, and non-toxic. In an embodiment, a useful moldable compound for making a dental floss holder may include a medical grade injection moldable plastic, such as ultrahigh molecular weight polyethylene (UHMWPE). In an embodiment, such materials enable the manufacturer to provide self tapping screws to accomplish the provision of threads in the threaded plastic parts. Consequently, any reference to threaded components is intended to include both the possibility of machining threads before assembly, or of providing threads during assembly by utilization of a self tapping fastener and a suitably sized aperature configured for such self tapping action upon assembly.

It is to be appreciated that the various aspects, features, structures, and embodiments of a dental floss holder as described herein is a significant improvement in the state of the art. The apparatus described is simple, reliable, and easy to use. Although only a few exemplary aspects and embodiments have been described in detail, various details are sufficiently set forth in the drawing figures and in the specification provided herein to enable one of ordinary skill in the art to make and use the invention(s), which need not be further described by additional writing.

Importantly, the aspects, features, structures, and embodiments described and claimed herein may be modified from those shown without materially departing from the novel teachings and advantages provided, and may be embodied in other specific forms without departing from the spirit or essential characteristics thereof. Therefore, the various aspects and embodiments presented herein are to be considered in all respects as illustrative and not restrictive. As such, this disclosure is intended to cover the structures described herein and not only structural equivalents thereof, but also equivalent structures. Numerous modifications and variations are possible in light of the above teachings. The scope of the invention, as described herein is thus intended to include variations from the various aspects and embodiments provided which are nevertheless described by the broad meaning and range properly afforded to the language herein, as explained by and in light of the terms included herein, or the legal equivalents thereof.

The invention claimed is:

1. A dental floss holder, comprising:
    (a) a body, said body comprising
        a spool case sized and shaped to accommodate a spool of dental floss of selected diameter, said spool case having sidewalls and a floor;
        a neck, said neck extending from said spool case generally along a first longitudinal axis;
        spaced apart first and second fingers extending outwardly from said neck, said first finger extending along a second longitudinal axis, said second longitudinal axis offset from said first longitudinal axis by an angle alpha ($\alpha$), and said second finger extending along a third longitudinal axis, said third longitudinal axis offset from said first longitudinal axis by an angle beta ($\beta$),
        said first and second fingers each extending outwardly from said neck to a respective distal end, and
        along at least a portion of the distal end of said first finger, a first floss guide, and
        along at least a portion of the distal end of said second finger, a second floss guide,
        said first finger extending back from its distal end to a knuckle, said knuckle providing a transition from said neck to said first finger, and further comprising at said knuckle, a knuckle floss guide;
        said second finger extending from its distal end to a bight, said bight providing a transition from said neck to said second finger
    (b) a cap, said cap sized and shaped to at least partially cover said spool case;
    (c) spaced apart first and second tensioning ledges provided on said cap; and
    (d) a clamp, said clamp comprising a compressible flange adapted for manually compressing and securing a length of dental floss against movement through said clamp during the use of said dental floss holder.

2. The apparatus as set forth in claim 1, wherein said neck comprises an obverse surface and a reverse surface, and wherein said reverse surface is tapered to decrease in thickness outward from said spool case.

3. The apparatus as set forth in claim 2, wherein said reverse surface of said neck comprises a curved shape.

4. The apparatus as set forth in claim 1, wherein said apart first and second tensioning ledges are laterally spaced apart on said cap.

5. The apparatus as set forth in claim 1, or in claim 4, wherein said first and second tensioning ledges are located spaced apart along a fourth axis, and wherein said fourth axis is not orthogonal to said first longitudinal axis.

6. The apparatus as set forth in claim 4, wherein said first and second tensioning ledges are integrally formed with said cap in a single part.

7. The apparatus as set forth in claim 1, wherein said cap further comprises an outer surface, said outer surface further comprising a pivot post upwardly protruding from outer surface for a height $H_1$.

8. The apparatus as set forth in claim 7, wherein said height $H_1$ is at least about three times the effective diameter D of a length of dental floss for use in said apparatus.

9. The apparatus as set forth in claim 8, wherein said pivot post comprises an annular shaped protrusion from said outer surface of said cap.

10. The apparatus as set forth in claim 9, wherein said pivot post further comprises annular threads therein.

11. The apparatus as set forth in claim 7, or in claim 9, or in claim 10, wherein said pivot post is integrally formed with said cap in a one-piece configuration.

12. The apparatus as set forth in claim 10, wherein said cap comprises a threaded bore concentric with said annular threads within said pivot post.

13. The apparatus as set forth in claim 11, wherein said cap comprises a threaded bore concentric with said annular threads within said pivot post.

14. The apparatus as set forth in claim 13, further comprising a spool post, said spool post sized and shaped for accommodating said spool for rotary movement of said spool about said spool post.

15. The apparatus as set forth in claim 14, wherein said spool post comprises an annular shaped structure of length $L_1$.

16. The apparatus as set forth in claim 15, wherein said spool post extends upward from said floor to an upper surface sized and shaped for securing mating engagement with said cap.

17. The apparatus as set forth in claim 16, wherein said upper surface of said spool post is a flat surface adapted for support of said cap.

18. The apparatus as set forth in claim 7, or in claim 9, or in claim 10, wherein said clamp comprises
    (a) a threaded fastener; and
    (b) a nut having threads adapted for tightening said nut with respect to said fastener, said nut having a shoulder portion complementary in size and shape to said pivot post.

19. The apparatus as set forth in claim 18, wherein said compressible flange extends outward from said shoulder portion.

20. The apparatus as set forth in claim 18, wherein said nut further comprises an upwardly extending grip portion.

21. The apparatus as set forth in claim 20, wherein said grip portion provides upward protrusions adapted for manually engaging and turning said nut.

22. The apparatus as set forth in claim 18, wherein said nut comprises an outer sidewall generally circular in shape.

23. The apparatus as set forth in claim 22, wherein said nut comprises an upper flanged surface, and wherein said grip portion is affixed at least in part to said upper flanged surface.

24. The apparatus as set forth in claim 23, wherein adjacent said outer sidewall, an undercut floss tensioning notch, defined by tensioning notch sidewalls, is provided between said grip portion and said upper flanged surface.

25. The apparatus as set forth in claim 22, wherein said outer sidewall further comprises a vertically extending floss receiving notch defined by floss receiving notch edgewalls.

26. The apparatus as set forth in claim 1, wherein said angle alpha ($\alpha$), and angle beta ($\beta$) are equal.

27. The apparatus as set forth in claim 1 or claim 26, wherein said neck and said first finger are coplanar.

28. The apparatus as set forth in claim 1 or claim 26, wherein said neck and said second finger are coplanar.

29. The apparatus as set forth in claim 1, further comprising a first finger outer floss guide portion, said first finger outer floss guide portion extending between said first floss guide and said knuckle floss guide, said first finger outer floss guide portion sized and shaped to accept and locate therein a length of dental floss.

30. The apparatus as set forth in claim 1, wherein said bight is sized and shaped to be complementary in size and shape to a human thumb, so as to accommodate thumb tensioning motion against a length of floss operably positioned between said second finger and said second tensioning ledge.

31. The apparatus as set forth in claim 1, wherein said bight is sized and shaped to be complementary in size and shape to a human index finger, so as to accommodate tensioning motion against a length of floss operably positioned between said second finger and said second tensioning ledge.

32. The apparatus as set forth in claim 1, wherein said cap further comprises a floss dispensing slot, said floss dispensing slot providing access between a spool of dental floss in said spool case and said clamp, so that dental floss may be withdrawn from said spool case for use.

33. The apparatus as set forth in claim 1, further comprising a dental floss cutter.

34. The apparatus as set forth in claim 32, wherein said dental floss cutter is affixed to said spool case.

35. A dental floss holder, comprising:
(a) a body, said body comprising
a spool case holding a supply of dental floss,
a cover for said spool case, said cover including a feed aperture therethrough from which dental floss is drawn from said spool case, said cover further comprising first and second tensioning ledges;
a neck extending outward from said spool case along a first longitudinal axis;
a pair of spaced apart fingers extending outwardly from said neck along second and third longitudinal axes, respectively, to distal ends, and sized and shaped to positing therebetween a working length of dental floss;
(b) a clamp, said clamp sized and shaped, in cooperation with said first and second tensioning ledges, for preventing movement of a section of floss in tensionable relationship with said working length of said dental floss, said clamp comprising a nut having a compressing flange, a receiving land, and a threaded fastener, said threaded fastener and said nut having threads of complementary working relationship, said nut further comprising at least one tensioning notch along a peripheral edge thereof.

36. The dental floss holder as set forth in claim 35, wherein said dental floss holder is sized and shaped to provide a bight between said neck and said second finger along which a length of dental floss is positionable for manual tensioning by a user.

37. The dental floss holder as set forth in claim 35, or in claim 36, wherein said dental floss holder is sized and shaped to provide an arcuate neck portion, between said first finger and said spool case, along which a second length of dental floss is positionable for manual tensioning by a user.

* * * * *

UNITED STATES PATENT AND TRADEMARK OFFICE
CERTIFICATE OF CORRECTION

PATENT NO. : 8,104,487 B2
APPLICATION NO. : 12/709449
DATED : January 31, 2012
INVENTOR(S) : Richard Hardy It is certified that error appears in the above-identified patent and that said Letters Patent is hereby corrected as shown below:

IN THE SPECIFICATION:

Column 4, line 4, after the words "first and", insert --second--.

Column 5, line 6, after the words "side perspective view of", delete "schematic view of".

Signed and Sealed this
Seventeenth Day of April, 2012

David J. Kappos
*Director of the United States Patent and Trademark Office*